US012698250B2

(12) United States Patent
Ye et al.

(10) Patent No.: US 12,698,250 B2
(45) Date of Patent: Aug. 4, 2026

(54) METHOD FOR PERFORMING MITSUNOBU REACTION BETWEEN ALCOHOLIC HYDROXYL GROUP DONOR AND ACTIVE HYDROGEN DONOR

(71) Applicant: Jiangsu Hecheng Advanced Materials Co., Ltd., Nanjing (CN)

(72) Inventors: Shouchen Ye, Nanjing (CN); Xiaolong Song, Nanjing (CN); Shuang Xu, Nanjing (CN); Liliang Zhao, Nanjing (CN)

(73) Assignee: Jiangsu Hecheng Advanced Materials Co., Ltd., Nanjing (CN)

( * ) Notice: Subject to any disclaimer, the term of this patent is extended or adjusted under 35 U.S.C. 154(b) by 580 days.

(21) Appl. No.: 18/033,595

(22) PCT Filed: Nov. 10, 2020

(86) PCT No.: PCT/CN2020/127698
§ 371 (c)(1),
(2) Date: Apr. 25, 2023

(87) PCT Pub. No.: WO2022/088244
PCT Pub. Date: May 5, 2022

(65) Prior Publication Data

US 2023/0399281 A1 Dec. 14, 2023

(30) Foreign Application Priority Data

Oct. 29, 2020 (CN) ......................... 202011183861.X

(51) Int. Cl.
*C07C 41/09* (2006.01)
*C07C 41/46* (2006.01)
*C07C 319/18* (2006.01)

(52) U.S. Cl.
CPC .............. *C07C 41/09* (2013.01); *C07C 41/46* (2013.01); *C07C 319/18* (2013.01)

(58) Field of Classification Search
USPC ........................................................... 568/598
See application file for complete search history.

(56) References Cited

U.S. PATENT DOCUMENTS

| | | | | |
|---|---|---|---|---|
| 2005/0159597 | A1 | 7/2005 | Ji et al. | |
| 2016/0161817 | A1 * | 6/2016 | Sasou ................ | C09K 19/3068 560/118 |
| 2017/0007686 | A1 | 1/2017 | Glick et al. | |

FOREIGN PATENT DOCUMENTS

| | | | |
|---|---|---|---|
| CN | 106132422 | A | 11/2016 |
| CN | 109207158 | A | 1/2019 |
| JP | 2008-1625 | A1 | 1/2008 |
| WO | 2017/090384 | A1 | 1/2017 |
| WO | 2020/179859 | A1 | 9/2020 |

OTHER PUBLICATIONS

Byrne et al. Sustain Chem Process (2016) 4:7.*
Liu, Dan et al., Mitsunobu reactions of aliphatic alcohols and bulky phenols, Tetrahedron Letters 55, 2014, pp. 3090-3092.

* cited by examiner

*Primary Examiner* — Ana Z Muresan
(74) *Attorney, Agent, or Firm* — Hoffmann & Baron, LLP

(57) ABSTRACT

A method for performing Mitsunobu reaction between an alcoholic hydroxyl group donor and an active hydrogen donor, comprising the following steps: reacting the alcoholic hydroxyl group donor and the active hydrogen donor with a trihydrocarbylphosphine reagent and an azodicarboxylate reagent in the presence of an organic solvent, wherein the organic solvent is a linear or branched alkane containing 8 to 16 carbon atoms.

10 Claims, No Drawings

METHOD FOR PERFORMING MITSUNOBU REACTION BETWEEN ALCOHOLIC HYDROXYL GROUP DONOR AND ACTIVE HYDROGEN DONOR

CROSS-REFERENCE TO RELATED APPLICATIONS

This application is the National Stage of International Application No. PCT/CN2020/127698, filed Nov. 10, 2020, which claims the benefit of Chinese Application No. 202011183861.X, filed Oct. 29, 2020, the contents of which is incorporated by reference herein.

TECHNICAL FIELD

The present application belongs to the field of organic synthesis and relates to a method for performing Mitsunobu reaction between an alcoholic hydroxyl group donor and an active hydrogen donor.

BACKGROUND ARTS

Mitsunobu reaction is a type of organic reaction with great application value invented by Japanese organic chemist O. Mitsunobu in 1967, refers to the intra- or intermolecular dehydration reaction between alcohol and acidic nucleophilic reagent precursors in the presence of trihydrocarbylphosphine and azodicarboxylate, and the reaction mechanism (taking triphenylphosphine and diethyl azodicarboxylate as reaction reagents and chiral alcohol as alcohol as an example) is generally as follows: triphenylphosphine and diethyl azodicarboxylate form an adduct, the proton of the nucleophilic reagent is removed, the alcohol and triphenylphosphine are bonded and activated, and the nucleophilic reagent undergoes $S_N2$ reaction to obtain the product, the reaction equation are following:

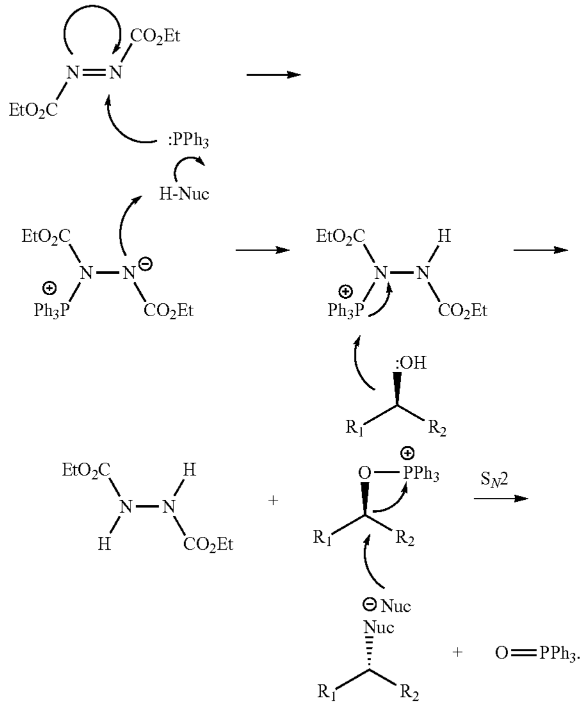

Mitsunobu reaction is typically carried out under mild neutral conditions. If a chiral alcohol participates in the reaction, the configuration of the carbon atom linked to the alcoholic hydroxyl group will generally be flipped and can be used to form a variety of chemical bonds, for example: chemical bond C—O, C—N, C—S, C—C and so forth. Therefore, Mitsunobu reaction is widely used in the total synthesis of various natural products or the conversion of the functional groups in compounds.

Mitsunobu reaction is a process of dehydration condensation. Therefore, the water in the reaction system must be controlled to avoid the losses of trihydrocarbylphosphine and azodicarboxylate. This type of reaction typically uses anhydrous aprotic solvent as a medium, such as toluene, tetrahydrofuran, ethyl tert-butyl ether, ethyl acetate, acetonitrile, dimethyl formamide, dimethyl acetamide, dichloromethane and so forth. These aprotic solvents have low flash point, strong smell, and are difficult to recover and are not in line with the present trend of green chemistry. At the same time, these solvents typically greatly affect the distribution, yield and post-treatment of the products, hence the optimization and selection of conditions for Mitsunobu reaction is a hot research topic in the green chemistry field nowadays.

According to the above reaction mechanism, the azodicarboxylate will eventually be converted into hydrazine dicarboxylate (such as

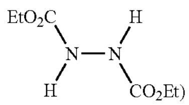

during Mitsunobu reaction process, and the hydrazine dicarboxylate will continue to react with the group of the alcoholic hydroxyl group donor with the hydroxyl group removed to obtain the following by-product:

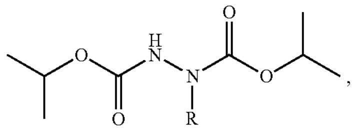

R represents the group of the alcoholic hydroxyl group donor with the hydroxyl group removed.

The above by-product is highly polarized and difficult to remove through conventional post-treatment methods, resulting in high end-product purification costs, significantly increases emissions of wastes and preparation costs, and affects the purity of the end-product as well as subsequent applications thereof.

Therefore, in this field, it is expected to develop a green method for Mitsunobu reaction with high yield, which can reduce the generation of hydrazine dicarboxylate by-products.

SUMMARY OF THE INVENTION

The purpose of the present application is to provide a method for performing Mitsunobu reaction between an alcoholic hydroxyl group donor and an active hydrogen donor. The method described in the present application can solve the problems in the prior art such as by-products being difficult to remove, large post-treatment wastes amount and low product purity existing in Mitsunobu reaction, and can effectively reduce the generation of hydrazine dicarboxylate by-products; the target product can be more easily separated from the reaction system with high reaction yield, convenient post-treatment, high product purity, no effect on the subsequent applications, and is environmentally friendly.

To achieve this purpose, the following technical solutions are used in the present application:

On the one hand, the present application provides a method for performing Mitsunobu reaction between an alcoholic hydroxyl group donor and an active hydrogen donor, the method specifically comprises the following steps:

performing reaction of the alcoholic hydroxyl group donor, the active hydrogen donor, a trihydrocarbylphosphine reagent and an azodicarboxylate reagent in the presence of an organic solvent to obtain the product of dehydration condensation of the alcoholic hydroxyl group donor and the active hydrogen donor;

wherein the organic solvent is a $C_{8-16}$ linear or branched alkane (for example, a C8, C10, C12, C14, C16 normal or isomeric alkane).

In the present application, the product of dehydration condensation of the above-mentioned alcoholic hydroxyl group donor with active hydrogen donor can be any compound of ethers, thioethers, esters, thioesters, amines and amides.

In this application, the generation of hydrazine dicarboxylate by-products can be effectively reduced through optimizing the reaction solvent system, and the target products can be more easily separated from the reaction system with high reaction yields, convenient post-treatment and high product purity.

In some embodiments of the present application, the organic solvent is any one or a combination of at least two of isomeric decane, isomeric dodecane, normal dodecane or isomeric pentadecane. Optionally, the organic solvent is isomeric dodecane.

In some embodiments of the present application, the alcoholic hydroxyl group donor is an organic substance containing an alcoholic hydroxyl group; the alcoholic hydroxyl group may be linked to at least one group of or combined structure of the groups of the follows: a substituted or unsubstituted linear alkyl, a substituted or unsubstituted branched alkyl, a substituted or unsubstituted cyclic alkyl, a substituted or unsubstituted aryl.

In some embodiments of the present application, the active hydrogen donor is an organic substance containing an active hydrogen group, wherein the active hydrogen group is selected from any one or a combination of at least two of —OH, —SH, —COOH, —COSH, $—NH_2$ or $—CONH_2$; the active hydrogen group may be linked to at least one group of or combined structure of groups of the follows: a substituted or unsubstituted C1-C12 linear alkyl, a substituted or unsubstituted C1-C12 branched alkyl, a substituted or unsubstituted C3-C12 cyclic alkyl, a substituted or unsubstituted C6-C12 aryl.

In some embodiments of the present application, the above C1-C12 alkyl may, for example, be methyl, ethyl, n-propyl, isopropyl, n-butyl, isobutyl, n-pentyl, isopentyl, n-hexyl, isohexyl and so forth; the above C3-C12 cyclic alkyl may, for example, be cyclopropyl, cyclobutyl, cyclopentyl, cyclohexyl, cycloheptyl and so forth; one or at least two $—CH_2—$ in the C1-C12 alkyl and C3-C12 cyclic alkyl are optionally independently replaced by any one of —O—, —S—, —CO—, —CS—, —CH═CH— or —C ≡C—, for example, one or at least two $—CH_2—$ may be independently replaced by any one of —O—, —S—, —CO—, —CS—, —CH═CH— or —C≡C—, or no $—CH_2—$ is replaced. For example, the group of ethyl with one $—CH_2—$ being replaced by —O— is methoxy, others can be analogized under the same logic and will no longer describe; the C6-C12 aromatic cyclic hydrocarbon group may for example be phenyl, substituted or naphthyl, and one or at least two —CH═ in the C6-C12 aromatic cyclic hydrocarbon group are optionally independently replaced by —N═, for example, one or at least two —CH═ may be independently replaced by —N═ (pyridyl, pyrimidinyl and so forth), or no —CH═ is replaced; one or at least two —H in the aromatic cyclic hydrocarbon group are optionally independently replaced by halogen, —CN, C1-C5 alkyl or C1-C5 alkoxy, for example, one or at least two —H may be independently replaced by halogen, —CN, C1-C5 alkyl or C1-C5 alkoxy, or no —H is replaced.

In some embodiments of the present application, the trihydrocarbylphosphine reagent is selected from any one or a combination of at least two of triphenylphosphine, tributylphosphine or trimethylphosphine.

In some embodiments of the present application, the azodicarboxylate reagent is selected from any one or a combination of at least two of diethyl azodicarboxylate, diisopropyl azodicarboxylate, bis-2-methoxyethyl azodicarboxylate, bis(4-chlorobenzyl) azodicarboxylate.

In some embodiments of the present application, the molar ratio of the alcoholic hydroxyl group donor and the active hydrogen donor is 1:1-1.2, for example, 1:1, 1:1.05, 1:1.1, 1:1.15, or 1:1.2.

In some embodiments of the present application, the molar ratio of the alcoholic hydroxyl group donor and the trihydrocarbylphosphine reagent is 1:1.05-1.3, for example, 1:1.05, 1:1.08, 1:1.1, 1:1.15, 1:1.2, 1:1.25, or 1:1.3.

In some embodiments of the present application, the molar ratio of the alcoholic hydroxyl group donor and the azodicarboxylate reagent is 1:1.05 to 1.3, for example, 1:1.05, 1:1.08, 1:1.1, 1:1.15, 1:1.2, 1:1.25, or 1:1.3.

In some embodiments of the present application, the reaction temperature is (for example, 30° C., 50° C., 80° C., 100° C., 110° C., or 120° C.) and the reaction duration is 1-12 h (for example, 1 h, 3 h, 5 h, 7 h, 9 h, 10 h, 11 h or 12 h).

In some embodiments of the present application, the material addition sequence of the reaction described in the present application is as follows: dropping the azodicarboxylate slowly into an organic solvent containing an alcoholic hydroxyl group donor, an active hydrogen donor, and a trihydrocarbylphosphine reagent, or, mixing the azodicarboxylate and the trihydrocarbylphosphine reagent first, and then adding the alcoholic hydroxyl group donor and the active hydrogen donor into the mixed liquid.

In some embodiments of the present application, the temperature during the dropping process is controlled at 30-120° C., such as 30° C., 50° C., 80° C., 100° C., 110° C. or 120° C.

In some embodiments of the present application, the reaction, including the raw material mixing process as well as reaction process, is carried out under inert gas protection.

In some embodiments of the present application, the reaction can be accelerated through ultrasound, microwave, or the addition of organic base (for example, triethylamine and so forth).

As an optional technical solution for the present application, the method specifically comprises the following steps:

performing reaction of an alcoholic hydroxyl group donor, an active hydrogen donor, a trihydrocarbylphosphine reagents and a azodicarboxylate reagent in the presence of an organic solvent at 30-120° C. for 1-12 h;

wherein the organic solvent is a $C_{8-16}$ linear or branched alkane;

the molar ratio of the alcoholic hydroxyl group donor and the active hydrogen donor is 1:1-1.2, and the molar ratio of the alcoholic hydroxyl group donor and the trihydrocarbylphosphine reagent is 1:1.05-1.3; the molar ratio of the alcoholic hydroxyl group donor and the azodicarboxylate reagent is 1:1.05-1.3.

Compared to the prior art, the present application has the following beneficial effects:

1. Compared with conventional anhydrous aprotic solvent, the choice of advanced saturated alkanes in the present application can effectively reduce the generation of reaction by-products, with higher product purity and no effect on the subsequent application of the products;
2. The products of the present application are more easily separated from the reaction system, reducing the economic cost and time cost of post-treatment;
3. The solvent used in the present application has high flash point, no smell, low danger, and more in line with the requirements of environment protection;

Therefore, using the green method of the present application of Mitsunobu reaction performed with the alcoholic hydroxyl group donor and the active hydrogen donor is conducive to industrial production and has high value for industrial application.

DETAILED EMBODIMENTS

The technical solutions of the present application are further described below through specific embodiments. It should be clear to the skilled artisan that the embodiments are merely for the understanding of the present application and should not be considered as any specific limitation on the present application.

In the following Examples and Comparative Examples, the related reagents are available from the market, wherein the GC test instrument is Agilent 7820A gas chromatograph, the MS test instrument is Agilent 7890B-5977A mass spectrometer, and the HPLC test instrument is Shimadzu LC-20AB high performance liquid chromatograph.

Example 1

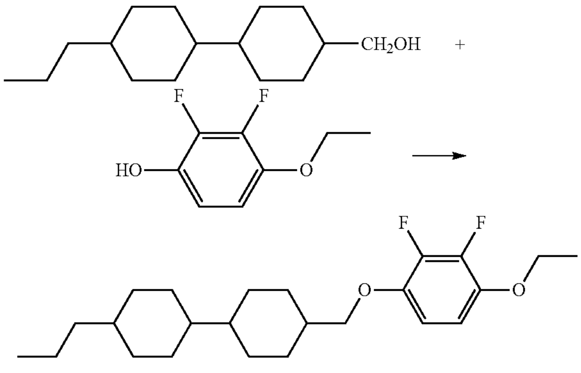

A

Adding 30 g (4'-propyl-[1,1'-bis(cyclohexane)]-4-yl) methanol, 23 g 4-ethoxy-2,3-difluorophenol, 35.31 g triphenylphosphine and 180 mL isomeric decane in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to 80° C. after dropping, and the reaction is carried out for 5 h. The reaction solution is filtered while it is hot, and the filtrate is frozen at −10° C. for 4 h. Filtering under reduced pressure and the filter cake is dried to give 38.4 g white solid, GC: 85.4%, yield: 77%.

MS data for compound A: 55 (5%), 69 (5%), 95 (5%), 146 (25%), 174 (50%), 220 (5%), 394 (5%).

The reaction equations for Examples 2-4 and Comparative Examples 1-2 below are the same as the equation for Example 1, with specific reaction conditions changed only.

Example 2

Adding 30 g (4'-propyl-[1,1'-bis(cyclohexane)]-4-yl) methanol, 23 g 4-ethoxy-2,3-difluorophenol, 35.31 g triphenylphosphine and 180 mL isomeric dodecane in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to 80° C. after dropping, and the reaction is carried out for 5 h. The reaction solution is filtered while it is hot, and the filtrate is frozen at −10° C. for 4 h. Filtering under reduced pressure and the filter cake is dried to give 43.1 g white solid, GC: 97.3%, yield: 86.8%.

Example 3

Adding 30 g (4'-propyl-[1,1'-bis(cyclohexane)]-4-yl) methanol, 23 g 4-ethoxy-2,3-difluorophenol, 35.31 g triphenylphosphine and 180 mL normal dodecane in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to 80° C. after dropping, and the reaction is carried out for 5 h. The reaction solution is filtered while it is hot, and the filtrate is frozen at −10° C. for 4 h. Filtering under reduced pressure and the filter cake is dried to give 42.3 g white solid, GC: 93.7%, yield: 85.2%.

Example 4

Adding 30 g (4'-propyl-[1,1'-bis(cyclohexane)]-4-yl) methanol, 23 g 4-ethoxy-2,3-difluorophenol, 35.31 g triphenylphosphine and 180 mL isomeric pentadecane in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to after dropping, and the reaction is carried out for 5 h. The reaction solution is filtered while it is hot, and the filtrate is frozen at −10° C. for 4 h. Filtering under reduced pressure and the filter cake is dried to give 41.7 g white solid, GC: 89.7%, yield: 84%.

Comparative Example 1

Adding 30 g (4'-propyl-[1,1'-bis(cyclohexane)]-4-yl) methanol, 23 g 4-ethoxy-2,3-difluorophenol, 35.31 g triphenylphosphine and 180 mL Toluene in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to 80° C. after dropping, and the reaction is carried out for 5 h. The reaction solution is rotary evaporated under reduced pressure to give light yellow solid. The solid is recrystallised in 150 mL of ethanol. Filtering under reduced pressure and the filter cake is dried to give 36.5 g white solid, GC: 77.4%, yield: 73.5%.

Comparative Example 2

Adding 30 g (4'-propyl-[1,1'-bis(cyclohexane)]-4-yl) methanol, 23 g 4-ethoxy-2,3-difluorophenol, 35.31 g triphenylphosphine and 180 mL DMF in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to 80° C. after dropping, and the reaction is carried out for 5 h. Adding 200 mL water and 200 mL dichloromethane into the reaction solution, stirring the mixture for 10 min for extraction and separating the liquid. Water phase is extracted with 200 mL dichloromethane twice, and the combined organic phase is wash with 200 mL water twice and is rotary evaporated under reduced pressure to give light yellow solid. The solid is recrystallised in 150 mL of ethanol. Filtering under reduced pressure and the filter cake is dried to give 39.1 g white solid, GC: 80.2%, yield: 78.7%.

Comparative Example 3

Adding 30 g (4'-propyl-[1,1'-bis(cyclohexane)]-4-yl) methanol, 23 g 4-ethoxy-2,3-difluorophenol, 35.31 g triphenylphosphine and 180 mL normal hexane in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to 80° C. after dropping, and the reaction is carried out for 5 h. The reaction solution is filtered while it is hot, and the filtrate is frozen at −10° C. for 4 h. Filtering under reduced pressure and the filter cake is dried to give 38.7 g white solid, GC: 81.2%, yield: 78%.

Comparative Example 4

Adding 30 g (4'-propyl-[1,1'-bis(cyclohexane)]-4-yl) methanol, 23 g 4-ethoxy-2,3-difluorophenol, 35.31 g triphenylphosphine and 180 mL cyclohexane in a 500 mL three-necked flask, evacuating air with nitrogen for three times, heating the mixture to 50° C. with stir, and dropping 28 g diisopropyl azodicarboxylate (DIAD) slowly into the above solution. The mixture is heated to 80° C. after dropping, and the reaction is carried out for 5 h. The reaction solution is filtered while it is hot, and the filtrate is frozen at −10° C. for 4 h. Filtering under reduced pressure and the filter cake is dried to give 35.2 g white solid, GC: 80.8%, yield: 71%.

Test for by-Product Content

The content of compound 4-((4-ethoxy-2,3-difluorophenoxy)methyl)-4'-propyl-1,1'-bis(cyclohexane) in above Examples 1-4 and Comparative Examples 1-2 is tested through HPLC method, the results are in Table 1 below.

TABLE 1

| | Content of impurity (%) |
|---|---|
| Example 1 | 3.18 |
| Example 2 | 0.52 |
| Example 3 | 1.21 |
| Example 4 | 2.16 |
| Comparative Example 1 | 4.65 |
| Comparative Example 2 | 2.859 |
| Comparative Example 3 | 4.57 |
| Comparative Example 4 | 5.12 |

It can be seen from Table 1 that the generation of impurity is significantly reduced through selecting a $C_{8-16}$ linear or branched alkane as organic solvent for Mitsunobu reaction as compared with the common aprotic solvents in the prior art, which is beneficial for improving the product purity.

Example 5

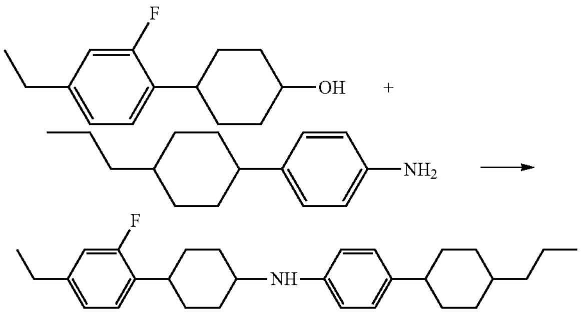

B

Adding 30 g 4-(4-ethyl-2-fluorophenyl)cyclohexanol, 30.8 g 4-(4-propylcyclohexyl)aniline, 37.17 g triphenylphosphine and 180 mL isomeric dodecane in a 500 mL three-necked flask, evacuating air with nitrogen for three times, heating the mixture to 50° C. with stir, and dropping 29.2 g diisopropyl azodicarboxylate (DIAD) slowly into the above solution. The mixture is heated to 100° C. after dropping, and the reaction is carried out for 5 h. The reaction solution is filtered while it is hot, and the filtrate is frozen at −10° C. for 4 h. Filtering under reduced pressure and the filter cake is dried to give 48.6 g white solid, GC: 91.4%, yield: 85.4%.

MS data for compound B: 123 (15%), 216 (55%), 392 (10%), 421 (20%).

Example 6

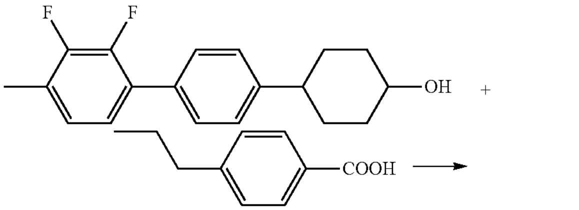

-continued

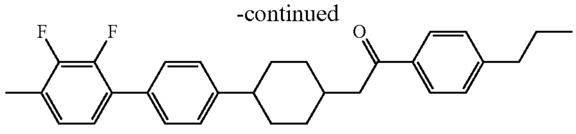

C

Adding 30 g 4-(2',3'-difluoro-4'-methyl-[1,1'-biphenyl]-4-yl)cyclohexanol, 17.11 g 4-propylbenzoic acid, 27.33 g triphenylphosphine and 180 mL isomeric dodecane in a 500 mL three-necked flask, evacuating air with nitrogen for three times, heating the mixture to 50° C. with stir, and dropping 21.47 g diisopropyl azodicarboxylate (DIAD) slowly into the above solution. The mixture is heated to 100° C. after dropping, and the reaction is carried out for 5 h. The reaction solution is filtered while it is hot, and the filtrate is frozen at −10° C. for 4 h. Filtering under reduced pressure and the filter cake is dried to give 40.6 g white solid, GC: 98.1%, yield: 91.2%.

MS data for compound C: 163 (35%), 244 (15%), 285 (25%), 419 (10%), 448 (15%).

Example 7

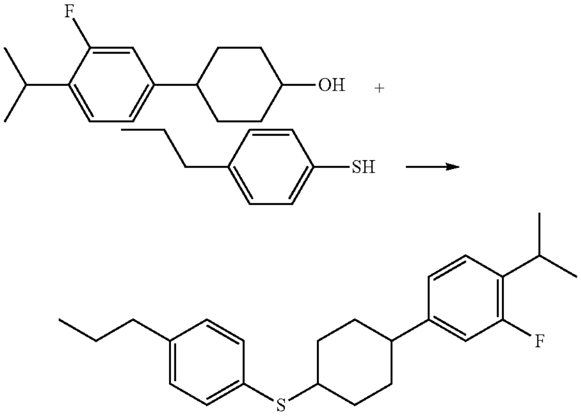

D

Adding 30 g 4-(3-fluoro-4-isopropylphenyl)cyclohexanol, 20.29 g 4-propylbenzenethiol, 34.96 g triphenylphosphine and 180 mL isomeric dodecane in a 500 mL three-necked flask, evacuating air with nitrogen for three times, heating the mixture to 50° C. with stir, and dropping 23.66 g diisopropyl azodicarboxylate (DEAD) slowly into the above solution. The mixture is heated to 80° C. after dropping, and the reaction is carried out for 5 h. The reaction solution is filtered while it is hot, and the filtrate is frozen at −10° C. for 4 h. Filtering under reduced pressure and the filter cake is dried to give 42.8 g white solid, GC: 97.6%, yield: 91%.

MS data for compound D: 137 (10%), 151 (45%), 327 (25%), 341 (10%), 370 (10%).

The applicant declares that the present application illustrates the process and method of the present application by means of the above examples, but the present application is not limited to the above examples, that is, it does not mean that the implement of the present application must rely on the above examples.

The invention claimed is:

1. A method for performing Mitsunobu reaction between an alcoholic hydroxyl group donor and an active hydrogen donor, which specifically comprises the following steps:

performing reaction of the alcoholic hydroxyl group donor, the active hydrogen donor, a trihydrocarbylphosphine reagent and an azodicarboxylate reagent in the presence of an organic solvent to obtain the product of dehydration condensation of the alcoholic hydroxyl group donor and the active hydrogen donor;

wherein, the organic solvent is a $C_{8-16}$ linear or branched alkane;

wherein the alcoholic hydroxyl group donor is selected from the group consisting of 4'-propyl-[1,1'-bis(cyclohexane)]-4-yl)methanol, 4-(4-ethyl-2-fluorophenyl)cyclohexanol, 4-(2',3'-difluoro-4'-methyl-[1,1'-biphenyl]-4-yl)cyclohexanol, and 4-(3-fluoro-4-isopropylphenyl)cyclohexanol; and wherein the active hydrogen donor is selected from the group consisting of 4-ethoxy-2,3-difluorophenol, 4-(4-propylcyclohexyl)aniline, and 4-propylbenzoic acid.

2. The method according to claim 1, wherein the organic solvent is selected from the group consisting of isomeric decane, isomeric dodecane, normal dodecane, and isomeric pentadecane.

3. The method according to claim 2, wherein, the organic solvent is isomeric dodecane.

4. The method according to claim 1, wherein, the trihydrocarbylphosphine reagent is selected from the group consisting of triphenylphosphine, tributylphosphine, and trimethylphosphine.

5. The method according to claim 1, wherein, the azodicarboxylate reagent is selected from the group consisting of diethyl azodicarboxylate, diisopropyl azodicarboxylate, bis-2-methoxyethyl azodicarboxylate, and bis(4-chlorobenzyl) azodicarboxylate.

6. The method according to claim 1, wherein, a molar ratio of the alcoholic hydroxyl group donor and the active hydrogen donor is 1:1-1.2;

optionally, the molar ratio of the alcoholic hydroxyl group donor and the trihydrocarbylphosphine reagent is 1:1.05-1.3;

optionally, the molar ratio of the alcoholic hydroxyl group donor and the azodicarboxylate reagent is 1:1.05-1.3.

7. The method according to claim 1, wherein, a reaction temperature is 30-120° C. and reaction duration is 1-12 h.

8. The method according to claim 1, wherein, material addition sequence of the reaction is as follows: dropping the azodicarboxylate slowly into an organic solvent containing an alcoholic hydroxyl group donor, an active hydrogen donor, and a trihydrocarbylphosphine reagent, or, mixing the azodicarboxylate and the trihydrocarbylphosphine reagent first, and then adding the alcoholic hydroxyl group donor and the active hydrogen donor into the mixed liquid;

optionally, temperature during the dropping process is controlled at 30-120° C.

9. The method according to claim 1, wherein, the reaction is carried out under inert gas protection;

optionally, adding an organic base in the reaction;

optionally, using ultrasound or microwave during the reaction process.

10. The method according to claim 1, comprising:

performing reaction of the alcoholic hydroxyl group donor, the active hydrogen donor, the trihydrocarbylphosphine reagent and the azodicarboxylate reagent in the presence of an organic solvent at 30-120° C. for 1-12 h to obtain the product of dehydration condensation of the alcoholic hydroxyl group donor and the active hydrogen donor;

wherein a molar ratio of the alcoholic hydroxyl group donor and the active hydrogen donor is 1:1-1.2, and a molar ratio of the alcoholic hydroxyl group donor and the trihydrocarbylphosphine reagent is 1:1.05-1.3; a molar ratio of the alcoholic hydroxyl group donor and the azodicarboxylate reagent is 1:1.05-1.3.

* * * * *